United States Patent [19]
Adams et al.

[11] Patent Number: 6,139,875
[45] Date of Patent: *Oct. 31, 2000

[54] AQUEOUS ENTERIC COATING COMPOSITION AND LOW GASTRIC PERMEABILITY ENTERIC COATING

[75] Inventors: Michael Wayne Adams, Holly Springs, N.C.; Stephen Hong-Wei Wu, Kingsport, Tenn.

[73] Assignee: Eastman Chemical Company, Kingsport, Tenn.

[*] Notice: This patent issued on a continued prosecution application filed under 37 CFR 1.53(d), and is subject to the twenty year patent term provisions of 35 U.S.C. 154(a)(2).

[21] Appl. No.: 09/162,282

[22] Filed: Sep. 29, 1998

[51] Int. Cl.⁷ ........................................................ A61K 9/42
[52] U.S. Cl. ............................ 424/476; 424/481; 424/482
[58] Field of Search ............................ 524/451; 424/476, 424/481, 482

[56] References Cited

U.S. PATENT DOCUMENTS

| | | | |
|---|---|---|---|
| 4,079,125 | 3/1978 | Sipos | 424/32 |
| 4,150,111 | 4/1979 | Warren | 424/35 |
| 5,026,559 | 6/1991 | Eichel | 424/458 |
| 5,104,922 | 4/1992 | Chang | 524/441 |
| 5,330,759 | 7/1994 | Pagay | 424/462 |
| 5,612,397 | 3/1997 | Gebhard | 524/35 |
| 5,733,575 | 3/1998 | Mehra et al. | |
| 5,756,008 | 5/1998 | Slutsky | 252/514 |

FOREIGN PATENT DOCUMENTS

| | | |
|---|---|---|
| 2057876 | 4/1981 | United Kingdom . |
| 95 16451 | 6/1995 | WIPO . |
| 97 03670 | 2/1997 | WIPO . |
| 97 48386 | 12/1997 | WIPO . |

OTHER PUBLICATIONS

Okhamafe & York, Int. J. Pharm.; 22 pp. 265–272 (1984).
O'Conner et al, Drug Dev. Ind. Pharm.; 18, 2123–2133 (1992).
Porter, Pharm. Tech.; Mar. 1980, 67–75.
Chatfield, The Science of Surface Coatings, pp. 453–454 (1962).
J. R. Bloor et al, Drug Dev. Ind. Pharm.; 15 (14–16), 2227–43 (1989).
R. K. Chang, Pharm. Tech.; 14 (10), 62–70 (1990).
J. W. Stafford, Drug Dev. Ind. Pharm.; 8(4) 513–30 (1982).
Parker et al, J. Pharm. Sci.; vol. 63, No. 1, 119–215 (1974).
Derwent Publications Ltd., London, GB; Class A1, AN 1996 –263781–XP002128219.
Derwent Publication Ltd., London, GB; Class A96, AN 1997 –095397 –XP002128220.
Derwent Publication Ltd., London,GB; Class A11, AN 1972 –82834T –XP002128221.

*Primary Examiner*—Paul R. Michl
*Attorney, Agent, or Firm*—Michael J. Blake; Harry J. Gwinnell

[57] ABSTRACT

Disclosed herein is an aqueous enteric coating composition comprised of a solution of a water-soluble salt of an enteric coating polymer, with a hydrophobic compound containing 12 to 20 carbon atoms and a water-insoluble solid flake material dispersed in the aqueous solution. The enteric coating formed from the present composition has good mechanical strength and shows superior resistance to attack by atmospheric moisture and simulated gastric fluid, while being readily broken down under the alkaline conditions which exist in the intestine.

16 Claims, 1 Drawing Sheet

AQUEOUS ENTERIC COATING COMPOSITION AND LOW GASTRIC PERMEABILITY ENTERIC COATING

FIELD OF THE INVENTION

The present invention relates to the field of enteric coating polymers. The present invention more particularly relates to the field of aqueous compositions of enteric coating polymers.

BACKGROUND OF THE INVENTION

It is frequently desirable to coat oral pharmaceutical tablet cores with an enteric coating. An enteric coating resists dissolution in acidic gastric media, but dissolves in the alkaline intestinal environment. Enteric coatings are useful for protecting the stomach wall from the effect of active ingredients in dosage form. For example, if aspirin is directly exposed to gastric mucosa, it can cause corrosion of the stomach wall. Enteric coatings are also used to protect active ingredients in the tablet core from chemical attack from stomach acids and digestive enzymes. Enteric coatings can also be used to promote the delivery of active ingredients in the core tablet to a particular region of the intestine such as the upper part of the small intestine, in order to enhance the bioavailability of the active ingredient.

Polymers useful as enteric coatings contain ionizable carboxylic groups and include cellulose acetate phthalates (C-A-P), cellulose acetate trimellitates(C-A-T), hydroxypropyl methyl cellulose phthalates(HPMCP), hydroxypropyl methyl cellulose acetate succinate (HPMCAS), polyvinyl acetate phthalate (PVAP), and certain acrylic polymers. In the low pH stomach environment, the carboxylic acid groups in the polymers remain un-ionized. Therefore, the polymeric coating remains insoluble in gastric fluid. The polymeric coating disintegrates or dissolves in the higher pH intestinal environment to allow dissolution of the tablet core in the small intestine. The active ingredients are absorbed through the intestinal wall for delivery to the blood stream.

Originally these polymers were applied to tablets as solutions in various organic solvents since the polymers are soluble in organic solvents. The use of organic solvents, however, is objectionable from environmental, physiological, and safety standpoints, as well as for economic reasons.

The use of organic solvents has been avoided by applying the polymers as aqueous solutions or dispersions of their water-soluble salts. The enteric polymers are water-solubilized with a water soluble base through neutralization of a sufficient number of carboxyl groups so that the polymer becomes water soluble or water dispersible. Useful water soluble bases include alkali metal hydroxides and ammonium hydroxide. The water soluble salts of enteric cellulose esters have been found to be somewhat hydrolytically unstable, hydrolyzing slowly upon exposure to atmospheric moisture or gastric juices. A resulting film of partly hydrolyzed polymer is partially insoluble in intestinal fluid, causing the active ingredient to be released too slowly in the intestinal tract.

Parker et al, *J. Pharm. Sci.* 63, 119–215(1974); Okhamafe & York, *Int. J. Pharm.* 22 (2–3) (1984), and Okhamafe & York (1984)disclose that the presence of solid filler material in film dispersed from a solution of a water soluble salt of an enteric polymer reduces polymer film hydrolysis.

Parker, et al disclose that the reduction in film hydrolysis is directly related to film thickness. However, a thicker film takes longer to disintegrate in the intestine. Similarly, Porter, *Pharm. Tech.*, March, 1980, pp 67–75, discloses that while low loadings of solid pigment material can somewhat increase film resistance to moisture, higher filler loading levels which would add more water resistance detrimentally affect the mechanical strength of the film. High tensile strength is required for a useful tablet coating. Therefore, the amount of solid filler material used for increasing water resistance is limited by decreased mechanical strength.

In light of the above, it would be desirable to provide an aqueous enteric coating composition containing a water soluble salt of a film-forming enteric polymer wherein the film coating provides a higher water resistance than was previously achievable and maintains good mechanical strength.

SUMMARY OF THE INVENTION

The present invention is an aqueous enteric coating composition which comprises a dispersion of about 5 to 45 weight percent of a hydrophobic compound having from about 12 to 20 aliphatic carbon atoms and about 5 to 50 weight percent of a water-insoluble flake material, dispersed in an aqueous solution of about 35 to 70 weight percent of a water-soluble salt of an enteric polymer, with the weight percentages being based on a total solids weight.

DETAILED DESCRIPTION OF THE INVENTION

Figure 1:
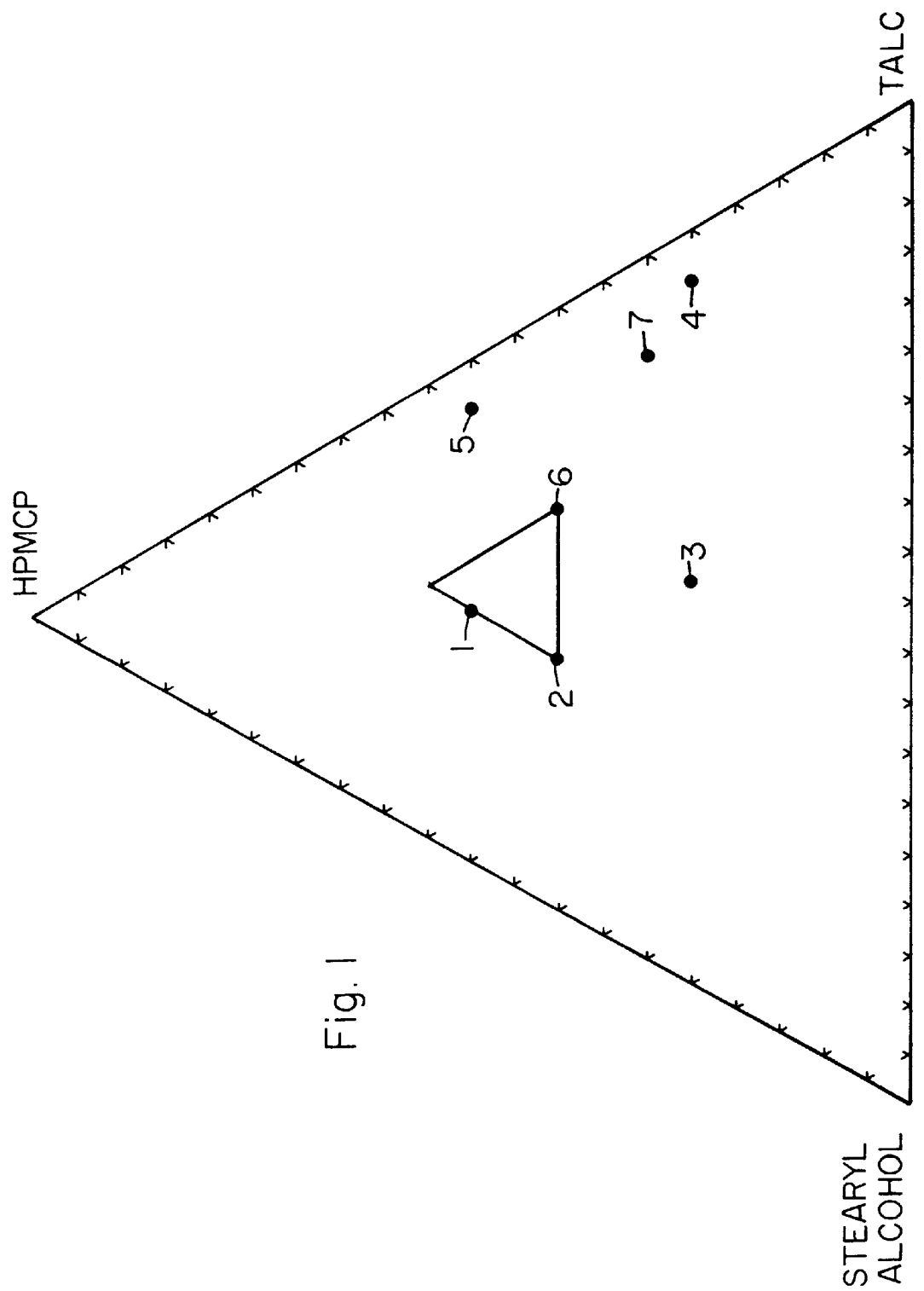
FIG. 1 is a triangular coordinate graph illustrating a preferred embodiment of the invention wherein the composition contains HPMCP, stearyl alcohol, and talc. The apex of the graph represents 100 weight percent HPMCP enteric polymer. The lower right corner of the graph represents 100 weight percent talc. The lower left hand corner represents 100 weight percent stearyl alcohol. Compositions containing various concentrations of those three components are represented graphically by the numerals 1–7 and correspond to coating compositions illustrated in Table 1.

The applicants discovered that, while maintaining good mechanical strength, the water and acid resistance of an enteric polymer film coating is increased beyond that which was previously achievable via solids loading by way of loading an aqueous solution of enteric polymer salt with a dispersion of a particular concentration of solid flake filler material and a hydrophobic compound containing aliphatic carbon atoms. Enteric coating compositions have not previously been loaded with a combination of solid flake material and hydrophobic aliphatic compound.

It was found that the present combination of flake material and hydrophobic aliphatic compound, within a particular concentration range, adds a "shingle effect" to the enteric coating. This shingle effect is evidenced by the fact that the moisture resistance provided is equivalent to that which would be provided by a coating containing a much higher percentage of solid filler. Since mechanical strength decreases with an increased concentration of solid filler, the present invention is beneficial in providing an increased water resistance without decreasing the mechanical strength of the coating. Additionally, the water resistant composition of the present invention can usefully be applied to a tablet as a relatively thin coat for the purpose of quick intestinal disintegration.

The aqueous enteric coating composition of the present invention comprises an aqueous dispersion of about 5 to 45 weight percent of a hydrophobic compound having between 12 to 20 aliphatic carbons and about 5 to 50 weight percent of a water-insoluble flake, dispersed in an aqueous solution comprising about 35 to 70 weight percent of a water soluble salt of an enteric polymer which dissolves only at a pH above about 5.0. The above listed weight percentages are based on the total weight of solids in the composition. The composition preferably contains a sufficient amount of water to provide a total solids content between about 5 to 20 weight percent, preferably between about 10 to 15 weight percent, based on the total weight of the composition.

The present composition comprises about 35 to 70 weight percent enteric polymer salt. The presence of more than about 70 weight percent polymer salt would provide a coating with insufficient resistance to water permeation in a gastric environment. But at least 35 weight percent enteric polymer is needed in order for a sufficient protective film to be formed around the tablet core and to hold the flake material and hydrophobic compound onto the core. The preferred concentration range of the soluble enteric polymer salt is about 40 to 55 weight percent.

An "enteric polymer" is herein defined as a polymer having a polystyrene equivalent weight average molecular weight (Mw) of about 50,000 to 150,000, and containing carboxyl groups which remain insoluble at a pH below about 4 (gastric pH range), but which ionize, and thus cause the polymer to dissolve, at a pH above about 5.0 (intestinal pH range). The enteric polymer used in the present composition is preferably a film-forming polymer. The most useful film-forming enteric polymers are cellulose acetate phthalate (C-A-P), cellulose acetate trimellitate (C-A-T), hydroxypropylmethylcellulose phthalate (HPMCP), copolymer of methacrylic acid and ethyl acrylate, hydroxypropylmethylcellulose acetate succinate (HPMCAS), and polyvinyl acetate phthalate (PVAP). The preferred Mw for HPMCP is between about 80,000 and 110,000, most preferably between 95,000 and 100,000. The preferred Mw for C-A-P is between about 55,000 and 75,000, with a Mw between 68,000 and 80,000 being more preferred.

A concentration of about 5 to 45 weight percent of a hydrophobic compound is dispersed throughout the present aqueous composition. The hydrophobic compound is a compound having 12 to 20 aliphatic carbon atoms. This hydrophobic component chemically repels aqueous, acidic medium away from the enteric polymer. At least 5 weight percent is needed to provide the shingle effect. The presence of more than 45 weight percent hydrophobic aliphatic compound causes agglomeration in the coating process. A concentration of about 20 to 35 weight percent hydrophobic compound is preferable.

The hydrophobic compound used may be any linear or branched chain compound having less than 1 percent solubility in water, a hydrophile-lipophile balance (HLB) value less than about 6, and which does not interfere chemically with the other components of the composition. The hydrophobic compound may contain non-aliphatic groups. Examples of such useful $C_{12}$ to $C_{20}$ hydrophobic compounds include alcohols, fatty acids and salts thereof, fatty amides and salts thereof, and lipids. A $C_{12}$ to $C_{20}$ alcohol is preferred, with stearyl alcohol being most preferred because of it's low toxicity.

The insoluble solid flake material dispersed throughout the aqueous composition of the present invention is present at a concentration of about 5 to 50 weight percent. More than about 50 weight percent solid flake material reduces the mechanical strength too much. A concentration of about 25 to 40 weight percent flake material is preferred.

The flake material (sheet-like) is water-insoluble, preferably an inorganic mineral. The more preferred flake material is one of the inert hydrous magnesium silicate materials referred to commonly as "talc" or pyrophyllite, which is essentially aluminum silicate having similar crystal structure and other properties to the talc materials. Other inert, powders whose crystals have a sheet-like or flake structure include materials such as aluminum flake, $TiO_2$ flakes, and silicate flakes.

It is a critical aspect of the present invention that the solid filler material has a flake or sheet-like shape. The shingle effect is most enhanced when the solid filler material is a flake material.

The average particle size of the flake material is preferably less than about 50 micrometers, with the average particle size being measured in equivalent circular diameters. It was a surprising aspect of the present invention to find that the water permeation barrier is further improved as the particle size of the solid flake material is decreased, using the same concentration of flake material. The preferred particle size of the flake material is less than about 10 micrometers, with a size less than about 1 micrometer (1,000 nanometers) being more preferable.

An exemplary embodiment of the preferred composition of the present invention is an approximately 10 percent solids content aqueous composition containing about 40 to 55 weight percent ammoniated HPMCP, with about 20 to 35 weight percent stearyl alcohol and about 25 to 40 weight percent talc dispersed therein, based on the total weight of solids. This particular composition is shown graphically by the smaller, triangular area indicated within FIG. 1.

Besides the insoluble flake material and hydrophobic compound of the present composition, the composition may also contain additive materials within the size range of about 0.1 to 100 micrometers. Additives used should be relatively hydrophobic. Plasticizers are especially useful for forming a flexible soft coating. Examples of suitable plasticizers include triacetin, diethyl phthalate (DEP), triethyl citrate (TEC), and dibutyl sebacate (DBS). Solid pigments may also be used. The weight percent of such additives should be less than about 15 weight percent, more preferably less than about 5 weight percent, based on the total weight of solids in the composition.

The present invention further includes a process of making an aqueous enteric coating composition comprising reacting about 35 to 70 weight percent of a enteric polymer with a solubilizing amount of a water-soluble base to provide an aqueous solution or dispersion of a salt of the enteric polymer and, dispersing about 5 to 45 weight percent of a hydrophobic compound having from about 12 to 20 aliphatic carbon atoms and about 5 to 50 weight percent of a water insoluble flake material in the aqueous polymer solution. The present process is preferably conducted under conditions providing a total solids content of about 5 to 20 weight percent solids. The water-insoluble components are preferably dispersed throughout the solution through high shear mixing using a homogenizer or a colloid mill.

The enteric polymer salt of the aqueous coating composition is preferably formed in situ by adding the non-ionized enteric polymer and a water-soluble base to the aqueous solution separately for reaction. Suitable water-soluble bases for neutralization of the polymer include $NH_4^+OH^-$, and alkali metal hydroxides, with ammonium hydroxide being the preferred neutralizing agent.

The aqueous enteric coating solution of the present invention is applied to a core substrate by any traditional coating means such as by spray coating. Suitable core substrates to which the aqueous enteric coating solution of the present invention can be applied includes pharmaceutically active tablets, pellets, granules, and beads. A coating weighing about 5 to 15 weight percent of the total coated core is preferable so that the core is fully coated, yet the coating is thin enough so that it dissolves quickly in the intestines. In order to protect the tablet cores from reacting with the basic coating solution, it is often preferable to apply a subcoat of polymer prior to applying the basic aqueous enteric coating solution of the present invention. For example, a polymer subcoat film weighing about 2 percent of the core table weight is useful.

In order for the polymer to demonstrate enteric properties in the gastric and intestinal media, a sufficient amount of ionized carboxyl salt groups must be converted back to the non-ionized free acid form. This can be done via different routes, depending on the exact polymer salt used. Heat may be applied to the coated tablets to convert the carboxylic acid groups into the free acid form upon evaporation of ammonia or water. Alternatively, the polymer carboxylic acid groups of the coated tablets can be reprotonated by treatment with an acid during production or by the gastric acid upon entry into the stomach environment.

The present invention further includes the enteric coating formed from the composition of the present invention. The coating of the present invention is preferably a film coating formed from a film-forming enteric polymer. The present coating dissolves only at a pH above about 5.0. The coating of the present invention may contain enteric polymer in the ionized salt form, enteric polymer in the protonated non-ionized enteric polymer form, or a combination thereof. The coating is formed upon evaporation of the water and other volatiles of the present aqueous composition. The components of the coating should be dispersed evenly throughout the coating in order to provide the maximum benefit.

The present invention further includes an enterically active dosage form, meaning that the active ingredient is released according to an enteric profile. The active dosage form of the present invention is a pharmaceutically active core enveloped by the enteric coating of the present invention. The core will typically contain an active ingredient and various excipients. Examples of useful pharmaceutically active ingredients for use in the present invention include aspirin, ibuprofen, ivermectin, acetaminophen, naproxen sodium, indomethacin, theophylline, propanolol, sucrose, erythromycin, pharmaceuticals such as diclofenac sodium, and the like. It is necessary that the tablet core is hard enough to resist attack by the coating solution and that it does not react with the components of the coating. Application of a sub-coating between the core and the enteric coating is useful in some situations so that the core does not react with the coating. The enterically active solid dosage form of the present invention preferably has a coating weighing between about 5 to 15 weight percent of the total coated dosage form so that the active core is adequately protected from water permeation, yet the active ingredient is released quickly enough in the intestines The following examples further illustrate the present invention, but should not be interpreted as a limitation thereon.

EXAMPLES

The materials and testing procedures used for the results shown herein are as follows:

Storage Stability Test

Accelerated storage stability evaluations were performed by placing the coated tablets in high density polyethylene bottles that contained a desiccant cartridge and were fitted with a tamper-proof seal. The bottles were placed in a glass desiccator over saturated sodium chloride solution. The desiccator and contents were stored in a 37° C. oven. The desiccator interior relative humidity was equilibrated at 75%.

Simulated Gastric Fluid Uptake Test

This evaluation was carried out as described in U.S. Pharmacopoeia XXII, pages 1784–1785 (1990). A total of 12 tablets were weighed and placed in a disintegration basket (Hanson Research Co.) and immersed in a pH 1.2 United States Pharmacopoeia simulated gastric fluid ("SGF") for 60 minutes. The tablets were then removed, surface dried, and weighed. The SGF uptake was calculated from the difference between the initial and final weight of the tablets divided by the initial weight.

Disintegration Time in Simulated Intestinal Fluid Test-After conducting the Simulated Gastric Fluid Uptake Test, the tablets were replaced in the baskets and immersed in USP simulated intestinal fluid of pH 6.8. The time to achieve disintegration of all twelve core tablets was recorded. All parts and percentages in the examples were calculated on a weight basis unless otherwise stated.

Examples 1–7

To prepare the coatings for Examples 1–7, a stock coating solution was first prepared. To prepare the stock solution, HPMCP (polystyrene equivalent Mw 96,000) was added to water and mixed with a laboratory stirrer. Triacetin plasticizer was then added and the mixture was stirred for 5 minutes. Then, a fully neutralizing amount of ammonium hydroxide (approximately 28%, aqueous) was added and the mixture was stirred for 30 minutes. The resulting stock solution contained 25 weight percent plasticizer (triacetin) and 12.4 weight percent ammonium hydroxide, based upon polymer weight.

Talc and stearyl alcohol were added to the stock coating solution to prepare Examples 1–7. Talc ($3MgO \cdot 4SiO_2 \cdot H_2O$) having average particle size of about 40 to 50 micrometers was added to the stock solution and the mixture was stirred for 5 minutes. Then a solution of stearyl alcohol in warm isopropyl alcohol was added with stirring. The mixture was passed through a colloid mill (Greerco, Model W200V). Each of the individual coating compositions prepared from the stock coating solution contained 13.8 weight percent solids.

500 gram tablet cores (7.3 weight percent diclofenac sodium, 92.7 weight percent excipients (59.7 wt % lactose, 24.8 wt % microcrystalline cellulose, and 8.2 wt % lubricants and other disintegrants) were sub-coated with a 13 weight percent solution of HPMCP in water to a level of 2 percent of the core tablet weight prior to application of the enteric coating, in order to protect the tablet cores from the basic coating solution. After the subcoat was allowed to dry, the aqueous enteric coating compositions prepared above were applied. Each aqueous coating composition prepared was applied in two different thicknesses, providing coatings weighing approximately 6 percent and 11 percent, based on the total weight of the coated tablet. Both the subcoat and the enteric coatings were applied by means of a fluid bed coater (STREA-1, manufactured by Niro-Aromatic, Inc., Columbia, Md.). The coating conditions were as follows:

|  | SUBCOAT | ENTERIC |
|---|---|---|
| Container Charge | 400 g | 400 g |
| Atomizer Pressure | 2.0 bar | 3 bar |
| Inlet Temp | 70° C. | 60° C. |
| Outlet Temp | 47° C. | 42° C. |
| Spray Rate | 14 mL/min | 15 mL/min |
| Spray Time | 4.3 min | 11 min for 6% coat |
|  |  | 22 min for 11% coat |

The Storage Stability Test was conducted on the tablets coated as described above. All of the coated tablets passed the disintegration test in simulated intestinal fluid after 3 months of storage under the accelerated storage conditions. This shows that the coatings formed from the aqueous composition of the present invention were stable under heat and humidity.

The coated tablets were tested to determine the effectiveness of films formed from the different aqueous enteric coating compositions. The effectiveness of the coating in protecting the active pharmaceutical from the action of simulated gastric fluid was determined by the Simulated Gastric Fluid Uptake Test. The effectiveness of the coating in allowing ready disintegration of the active pharmaceutical in simulated intestinal fluid was determined by conducting the Dissolution Test in Simulated Intestinal Fluid. The results of these tests are shown illustrated Table 1.

The test results in Table 1 show, at two different coating thickness levels, the number of tablet coatings (18 tablet samples were tested for each example) that completely failed in Simulated Gastric Fluid. "Failure" means that the coating broke away from the tablet so that the tablet was not protected. Failure is due to low mechanical strength. A failure of more than 3 out of 18 was considered to be unacceptable. The % SGF Uptake results show the weight percent of simulated gastric fluid absorbed by the coated tablets. The higher SGF uptake causes the tablet to loose efficacy. About 10 weight percent SGF uptake is acceptable. The intestinal disintegration time after being exposed to gastric fluid is also shown. It is desirable for the intestinal disintegration time to be short.

The results shown in Table 1 indicate the boundaries of the particular useful concentration of polymer, talc, and stearyl alcohol. The results show that both an approximately 6 weight percent coating and an approximately 12 weight percent coating are useful, depending specifically on the coating composition.

The importance of combining talc and stearyl alcohol in the particular concentration ranges of the present invention can be seen by comparing the Examples, as follows:

Examples 1, 1a, 2, 2a, 6, and 6a illustrate coating compositions within the scope of the present invention and provided tablet coatings having few failures in simulated gastric fluid. The gastric uptake in those examples was less than 10%. Example 6 illustrates that the 5.9 weight percent coating did not fully cover the core tablet.

Example 5a illustrates that the lower concentration limit for stearyl alcohol is near 5 weight percent. Since 0 tablets failed in the disintegration test yet the average uptake was 13%, this indicates that the stearyl alcohol concentration was not quite sufficient when combined with 50 weight percent HPMCP and 45 weight percent talc.

Examples 3, 3a, 7, and 7a demonstrate that neither a 25% or 30% enteric polymer concentration is sufficient to hold the talc and stearyl alcohol.

Examples 4 and 4a demonstrate that 75% talc reduced the mechanical strength of the coating, evidenced by the high number of mechanical failures in simulated gastric fluid.

Example 8

In an experiment similar to Examples 1–7, C-A-P was used as the enteric polymer instead of HPMCP, and aspirin was the substrate. A coating which contained 40% of C-A-P, 23% of stearyl alcohol, and 27% of talc exhibited lower SGF uptake (4%) than coatings which contained 48% C-A-P, 12% stearyl alcohol, and 27% talc (7% SGF uptake); 60% C-A-P, 12% stearyl alcohol, and 12% talc (8% SGF uptake); or 50% C-A-P, 23% stearyl alcohol, and 12% talc (6% SGF uptake).

TABLE 1

RESULTS FROM EXAMPLES 1–7

| | Coating Composition | | | | Gastric | | |
|---|---|---|---|---|---|---|---|
| Ex. | HPMCP (wt %) | Stearyl Alcohol (wt %) | Talc (wt %) | Coating Weight (wt. %) | SGF Failure (#tabs) | SGF Uptake (wt %) | Intestinal Disintegration (minutes) |
| C-1 | 100 | 0 | 0 | 6.3 | 18/18 | 99 | 2 |
| C-2 | 100 | 0 | 0 | 12.6 | 18/18 | 31 | 2 |
| 1 | 50 | 25 | 25 | 5.5 | 3/18 | 13.0 | 2.50 |
| 1a | 50 | 25 | 25 | 11.54 | 0/18 | 7.5 | 2.75 |
| 2 | 40 | 35 | 35 | 7.0 | 3/18 | 6.0 | 2.5 |
| 2a | 40 | 35 | 35 | 11.4 | 1/18 | 6 | 4.0 |
| 3 | 25 | 35 | 40 | 6.5 | 18/18 | n/a | n/a |
| 3a | 25 | 35 | 40 | 10.9 | 6/18 | 1.71 | 8.0 |
| 4 | 25 | 5 | 70 | 6.3 | 18/18 | n/a | n/a |
| 4a | 25 | 5 | 70 | 10.7 | 18/18 | n/a | n/a |
| 5 | 50 | 5 | 45 | 5.7 | 8/18 | 14.9 | |
| 5a | 50 | 5 | 45 | 10.5 | 0/18 | 13.0 | 2.5 |
| 6 | 40 | 20 | 40 | 5.9 | 10/18 | 9.9 | 2.3 |

TABLE 1-continued

RESULTS FROM EXAMPLES 1–7

| | Coating Composition | | | | Gastric | | |
|---|---|---|---|---|---|---|---|
| Ex. | HPMCP (wt %) | Stearyl Alcohol (wt %) | Talc (wt %) | Coating Weight (wt. %) | SGF Failure (#tabs) | SGF Uptake (wt %) | Intestinal Disintegration (minutes) |
| 6a | 40 | 20 | 40 | 11.1 | 0/18 | 7.1 | 4.0 |
| 7 | 30 | 10 | 60 | 6.8 | 18/18 | n/a | n/a |
| 7a | 30 | 10 | 60 | 11.2 | 17/18 | n/a | n/a |

The data from Table 1 was compiled in a triangular coordinate graph shown in FIG. 1. The data points were used to plot out an area within which the preferred composition concentrations of HPMPC, stearyl alcohol, and talc were outlined. The area mapped out in the triangular coordinate graph corresponds to a preferred composition comprising between about 40 to 55 weight percent HPMCP, between about 20 to 35 weight percent stearyl alcohol, and between about 25 to 40 weight percent talc.

We claim:

1. An aqueous enteric coating composition comprising: a dispersion of about 5 to 45 weight percent of a hydrophobic compound having from about 12 to 20 carbon atoms selected from the group consisting of alcohols, fatty acids and salts thereof, fatty amides and salts thereof, and lipids and about 5 to 50 weight percent of a water-insoluble flake material, dispersed in an aqueous solution of about 35 to 70 weight percent of a water-soluble salt of an enteric polymer selected from the group consisting of cellulose acetate phthalate (C-A-P), cellulose acetate trimellitate (C-A-T), hydroxypropyl methylcellulose phthalate (HPMCP), methacrylic acid/ethyl acrylate copolymer, hydroxypropyl methylcellulose acetate succinate (HPMCAS), and polyvinyl acetate phthalate (PVAP), wherein said weight percentages are based on a total solids weight.

2. The enteric coating of claim 1 wherein the concentration of said water-soluble salt of an enteric polymer is about 40 to 55 weight percent, the concentration of said hydrophobic compound is about 20 to 35 weight percent, and the concentration of said flake material is about 25 to 40 weight percent, based on the total solids weight.

3. The composition of claim 1 wherein a sufficient amount of water is present so that said composition has a total solids content of about 5 to 20 weight percent, based on the total weight of said composition.

4. The composition of claim 1 wherein said hydrophobic compound is stearyl alcohol.

5. The composition of claim 1 wherein said flake material is a talc.

6. The composition of claim 1 wherein said flake material has an average particle size less than about 50 micrometers.

7. The composition of claim 6 wherein said flake material has an average particle size less than about 10 micrometers.

8. The composition of claim 7 wherein said flake material has an average particle size less than about 1 micrometer.

9. The composition of claim 1 further comprising up to about 15 weight percent of an additive having a particle size between 0.1 to 100 micrometers, wherein the summation of all solids weight percentages equals 100 weight percent.

10. A process of making an aqueous enteric coating composition comprising:
providing as aqueous solution of about 35 to 70 weight percent of an enteric polymer selected from the group consisting of cellulose acetate phthalate (C-A-P), cellulose acetate trimellitate (C-A-T), hydroxypropyl methylcellulose phthalate (HPMCP), methacrylic acid/ethyl acrylate copolymer, hydroxypropyl methylcellulose acetate succinate (HPMCAS), and polyvinyl acetate phthalate (PVAP); and dispersing about 5 to 45 weight percent of a hydrophobic compound having from about 12 to 20 aliphatic carbon atoms selected from the group consisting of alcohols, fatty acids and salts thereof, fatty amides and salts thereof, and lipids and about 5 to 50 weight percent of a water-insoluble flake material into said aqueous solution, with said weight percentages based on a final total solids weight.

11. The process of claim 10 wherein said dispersing step is conducted in the presence of about 80 to 95 weight percent water, based on a total composition weight.

12. An enteric coating comprising a blend of about 35 to 70 weight percent of an enteric polymer selected from the group consisting of cellulose acetate phthalate (C-A-P), cellulose acetate trimellitate (C-A-T), hydroxypropyl methylcellulose phthalate (HPMCP), methacrylic acid/ethyl acrylate copolymer, hydroxypropyl methylcellulose acetate succinate (HPMCAS), and polyvinyl acetate phthalate (PVAP), about 5 to 45 weight percent of a hydrophobic compound having from about 12 to 20 aliphatic carbon atoms selected from the group consisting of alcohols, fatty acids and salts thereof, fatty amides and salts thereof, and lipids, and about 5 to 50 weight percent of a water-insoluble flake material.

13. The enteric coating of claim 12 wherein said water-insoluble flake material has a particle size less than about 50 micrometers.

14. The enteric coating of claim 13 wherein said water-insoluble flake material has a particle size less than about 1 micrometer.

15. An enterically active solid dosage form comprising a pharmaceutically active core enveloped by an enteric coating composition comprising a blend of about 35 to 70 weight percent of an enteric polymer selected from the group consisting of cellulose acetate phthalate (C-A-P), cellulose acetate trimellitate (C-A-T), hydroxypropyl methylcellulose phthalate (HPMCP), methacrylic acid/ethyl acrylate copolymer, hydroxypropyl methylcellulose acetate succinate (HPMCAS), and polyvinyl acetate phthalate (PVAP), about 5 to 45 weight percent of a hydrophobic compound having from about 12 to 20 aliphatic carbon atoms selected from the group consisting of alcohols, fatty acids and salts thereof, fatty amides and salts thereof, and lipids, and about 5 to 50 weight percent of a water-insoluble flake material.

16. The solid dosage form of claim 15 wherein the weight of said enteric coating is about 5 to 15 weight percent of the total weight of said solid dosage form.

* * * * *